(12) United States Patent
Duchesne et al.

(10) Patent No.: US 6,180,362 B1
(45) Date of Patent: Jan. 30, 2001

(54) PEPTIDES WHICH INHIBIT RAS PROTEIN ACTIVITY, THEIR PREPARATION AND USE

(75) Inventors: Marc Duchesne, Sucy-en-Brie; Fabien Schweighoffer, Vincennes; Bruno Tocque, Paris, all of (FR)

(73) Assignee: Rhone-Poulenc Rorer S.A., Antony (FR)

( * ) Notice: Under 35 U.S.C. 154(b), the term of this patent shall be extended for 0 days.

(21) Appl. No.: 08/379,580

(22) PCT Filed: Jul. 28, 1993

(86) PCT No.: PCT/FR93/00772

§ 371 Date: Apr. 24, 1995

§ 102(e) Date: Apr. 24, 1995

(87) PCT Pub. No.: WO94/03597

PCT Pub. Date: Feb. 17, 1994

(30) Foreign Application Priority Data

Jul. 30, 1992 (FR) .................................................. 92-09433

(51) Int. Cl.[7] ........................... C12P 21/06; C07H 21/04; A61K 38/00
(52) U.S. Cl. ........................ 435/69.1; 435/320.1; 514/2; 514/44; 530/300; 530/350; 536/23.5; 536/24.3; 536/24.31
(58) Field of Search ..................................... 530/300, 350; 536/23.1, 24.5; 514/2, 44

(56) References Cited

U.S. PATENT DOCUMENTS

| | | |
|---|---|---|
| 5,585,479 | 12/1996 | Hoke et al. . |
| 5,726,155 * | 3/1998 | Bokoch et al. ........................ 514/13 |
| 5,760,203 * | 6/1998 | Wong et al. ........................ 536/23.1 |
| 5,763,573 * | 6/1998 | McCormick et al. ............... 530/326 |

OTHER PUBLICATIONS

Levrero et al. (1991) Gene 101:195.*

Danos & Mulligan (1988) PNAS 85:6460.*

Milligan et al., Current Concepts in Antisense Drug Design, Journal of Medicinal Chemistry, 36(14), 1923–1937 (1993).

Westermann et al., Inhibition of expression of SV40 virus large T–antigen by antisense oligodeoxyribonucleotides*, Biomed. Biochim. Acta. 48(1) 85–93 (1989).

Bennett, Antisense Research, Science 271, 434 (1996).

* cited by examiner

*Primary Examiner*—Kenneth R. Horlick
(74) *Attorney, Agent, or Firm*—Finnegan, Henderson, Farabow, Garrett & Dunner, L.L.P.

(57) ABSTRACT

Peptides capable of inhibiting the transforming activity of activated p21 proteins, their preparation and compositions containing them are disclosed. Particular regions of the GAP protein have been identified and characterized that are involved in the transduction of activation signals of p21 proteins. Peptides derived from GAP protein but carrying an effector region rendered non-functional have been shown to inhibit the p21 signaling route. The products according to the invention are useful in pharmaceutical compositions to inhibit the transformation activity of ras genes whose transformation proceeds by a functional p21-GAP interaction.

44 Claims, 3 Drawing Sheets

PEPTIDES WHICH INHIBIT RAS PROTEIN ACTIVITY, THEIR PREPARATION AND USE

The present invention relates to new peptide and nucleotide sequences and their pharmaceutical use. More particularly, the present invention relates to new peptides which are capable of at least partly inhibiting the transformation activity of ras proteins.

Various genes, called oncogenes and suppressor genes, are involved in the control of cell division. Among these, the ras genes, and their products generally called p21 proteins, play a key role in control of cell proliferation in all eukaryotic organisms where they have been researched. In particular, it has been demonstrated that certain specific modifications of these proteins cause them to lose their normal control and leads them to become oncogenic. A large number of human tumours have thus been associated with the presence of modified ras genes. Furthermore, excessive expression of these p21 proteins may lead to a dysregulation in cell proliferation. Understanding of the exact role of these p21 proteins in the cells, their mode of functioning and their characteristics thus constitutes a major part in the understanding of and therapeutic approach to carcinogenesis.

In vivo, the precise nature of the events responsible for activation of p21 proteins and transduction of the signal which they carry is still not known. It is known that they perform their function by oscillating between two states of conformation: an inactive form bonded to GDP and an active form bonded to GTP. The activity of these proteins is thus controlled by factors which govern the equilibrium between these two forms, that is to say the transition p21-GDP→p21-GTP and vice versa.

As regards activation of the p21-GDP complexes, recent works report physiological situations in the course of which the proportion of ras proteins bonded to GTP increases in the cell. These are activation of T lymphocytes and stimulation of 3T3 fibroblasts by growth factors such as EGF and PDGF. This increase in the proportion of p21-GTP may be explained at least in part by the action of a protein which plays a role analogous to that of a receptor for the G transduction proteins. In this respect, certain proteins which are capable of promoting the exchange of GDP on p21 proteins have been identified, originating from the brains of cattle (West et al., FEBS Lett. 259 (1990) 245) and rats (Wolfman and Macara, Science 248 (1990) 67). The distinct cell location of these factors and the very different experimental conditions under which they have been obtained suggests that the proteins are different. They are active both on normal ras proteins and on those which are oncogenic. These activities have been classified under the name GEF: Guanide nucleotide Exchange Factor.

As regards the inactivation of the p21-GTP complexes, a cytosol protein having the power greatly to accelerate hydrolysis of the GTP bonded to the p21 protein has been discovered (Trahey and McCormick, Science 238 (1987) 542). This protein, called GAP, interacts with the p21 proteins in a catalytic manner and multiplies the rate of hydrolysis of GTP by 100 to 200, measured in vitro for the normal p21 protein. Various works have demonstrated that the catalytic domain of this protein of about 1044 amino acids was situated in the carboxy-terminal region (residues 702–1044), and that this region was responsible for the interaction of the GAP protein with the p21 proteins (cf. WO91/02749).

However, the role of this GAP protein has not yet been elucidated clearly. In particular, the elements and factors which allow transduction of the activation signals of the p21 proteins to the cell are not known. The present invention results from the discovery by the Applicant that the GAP protein is not simply a regulator having as its sole role deactivation of p21, causing it to pass into the inactive state as the result of hydrolysis of GTP, but that it is also the effector of p21 proteins triggering the cell response. The present invention more particularly results from the identification and characterization of particular regions (so-called effector regions) of the GAP protein which are involved in the transduction of activation signals of p21 proteins. The discovery of the existence of such a region and its characterization enable new peptides which can be used pharmaceutically to be prepared.

The invention thus first relates to peptides which are capable of at least partly inhibiting the transformation activity of activated p21 proteins. It is understood that the term p21 protein designates any expression product of a normal or oncogenic ras gene.

More particularly, the invention relates to peptides which are capable of at least partly inhibiting the transformation activity of p21-GTP-GAP complexes. It is furthermore known that p21 proteins are necessary for expression of the transformation power of oncogenes acting upstream, such as src, HER1, HER2 and the like. As a result, the peptides according to the invention and any pharmaceutical composition comprising them can also be used for treatment of tumours having these activated genes.

The peptides according to the invention are preferably derivatives of the GAP protein.

In the context of the present invention, the term derivative designates any molecule obtained by modification of a genetic and/or chemical nature, the required inhibition capacity being preserved. Modification of a genetic and/or chemical nature may be understood as meaning any mutation, substitution, deletion, addition and/or modification of one or more residues. Such derivatives may be generated for various purposes, such as, in particular, that of increasing the affinity of the peptide for its interaction site, that of improving its production levels, that of increasing its resistance to proteases or of improving its passage through the cell membranes, that of increasing its therapeutic efficacy or of reducing its secondary effects, or that of conferring on it new pharmacokinetic and/or biological properties.

Peptides derived from the protein GAP which may be mentioned are, in particular, any peptide which is capable of bonding the p21 protein, if appropriate complexed with GTP, but carrying an effector region rendered non-functional. Such peptides may be obtained by deletion, mutation or disruption of this effector region on the protein GAP.

The peptides according to the invention more preferably comprise all or part of the peptide sequence SEQ ID No. 2 or of a derivative thereof.

The term derivative has the same meaning as above.

The peptides according to the invention may thus have the structure of the peptide of sequence SEQ ID No. 2, of a fragment thereof, or a structure derived therefrom (for example a peptide incorporating the peptide SEQ ID No. 2). Such peptides may be generated in various ways. In particular, they may be synthesized by a chemical route, on the basis of the sequence SEQ ID No. 2, using peptide synthesizers known to the expert. They may also be synthesized by a genetic route, by expression of a nucleotide sequence coding for the required peptide in a cell host, possibly followed by chemical or enzymatic modifications. In the case of synthesis by a genetic route, the nucleotide sequence may be prepared chemically using an oligonucleotide synthesizer, on the basis of the peptide sequence given in the present Application and of the genetic code. The nucleotide sequence may also be prepared from the nucleotide sequence given in the present Application (SEQ ID No. 1), by enzymatic cutting, ligation, cloning and the like, in accordance with techniques known to the expert. These peptides may also be modified by addition of sequences allowing them a precise cell location. In particular, sequences of the type CAAX, where C is a cysteine, A is an aliphatic amino acid and X is any amino acid, enabling determination of whether a peptide is or is not modified after transduction by a cell farnesyl transferase, may be added (Cancer Cells Vol. 3(9) 1991, 331).

The present invention thus allows generation of peptides derived from the protein GAP and, more particularly, from the sequence SEQ ID No. 2 which have properties of biological interest with regard to pharmaceutical use. The biological activity of these various peptides according to the invention may be evaluated in accordance with various tests described in the examples, and in particular by a test for maturation of oocytes.

Other peptides according to the invention are the peptides which are capable of entering into competition with the peptides defined above for interaction with their cell target. Such peptides may be synthesized in particular on the basis of the sequence of the peptide in question, and their capacity to enter into competition with the peptides defined above for interaction with their cell target may be determined as described in the examples.

Examples of peptides according to the invention which may be mentioned are the peptides having the following amino acid sequence:

peptide having the sequence SEQ ID No. 2, peptide PVEDRRRVRAI, SEQ ID No. 10 (positions 5–15 on the sequence SEQ ID No. 2)

peptide EISF, SEQ ID No. 11 (positions 26–29 on the sequence SEQ ID No. 2)

peptide EDGWM, SEQ ID No. 12 (positions 42–46 on the sequence SEQ ID No. 2)

protein GAP carrying an effector region rendered non-functional, polypeptides P4–P9 (SEQ ID Nos. 4–9) described in Example 2, peptides in competition with the above peptides.

The invention also provides non-peptide compounds or compounds which are not exclusively peptide compounds which can be used pharmaceutically. It is in fact possible, from the active protein patterns described in the present Application, to realize molecules which inhibit the signalling route dependent on the protein GAP, which are not exclusively peptide molecules and which are comparable with pharmaceutical use.

The present invention also relates to any nucleotide sequence coding for a peptide according to the invention. It may be, in particular, a sequence comprising all or part of the sequence SEQ ID No. 1 or a sequence derived therefrom. Derived sequence is understood in the context of the present invention as any sequence hybridizing with the sequence SEQ ID No. 1 or with a fragment thereof and coding for a peptide according to the invention, as well as the sequences resulting from the latter by degeneration of the genetic code. An example of a sequence according to the invention hybridizing with the sequence SEQ ID No. 1 is shown on the sequence SEQ ID No. 3. The sequences according to the invention may be used for production of the peptides according to the invention. In this case, the part coding for the said peptide is generally placed under the control of signals which allow its expression in a cell host. The choice of these signals (promoters, terminators, "leader" sequence for secretion and the like) may vary according to the cell host used. In addition, the nucleotide sequences according to the invention may form part of a vector, which may be of autonomous or integrated replication. More particularly, vectors of autonomous replication may be prepared by using sequences of autonomous replication in the host chosen. As regards integrating vectors, these may be prepared, for example, by using sequences homologous to certain regions of the host genome, allowing integration of the vector by homologous recombination. The cell hosts which can be used for production of peptides according to the invention by the recombinant route are either eukaryotic hosts or prokaryotic hosts. Among the eukaryotic hosts which are suitable, there may be mentioned animal cells, yeasts or fungi. Yeasts which may be mentioned in particular are yeasts of the genus Saccharomyces, Kluyveromyces, Pichia, Schwanniomyces or Hansenula. Animal cells which may be mentioned are the cells COS, CHO, C127 and the like. Among the fungi there may be mentioned more particularly Aspergillus ssp. or Trichoderma ssp. The following bacteria—*E. coli*, Bacillus or Streptomyces—are preferably used as prokaryotic hosts.

The nucleotide sequences according to the present invention can also be used in the pharmaceutical field, either in the context of gene therapy or for detection, by hybridization experiments, of the expression of GAP genes in biological samples, or for preparation of antisense oligonucleotides. As regards gene therapy, the sequences according to the invention may be inserted into vectors, such as retroviral vectors or adenoviral vectors, enabling them to be administered in vivo (Médicine et Sciences 7 (1991) 705).

The various nucleotide sequences according to the invention may or may not be of artificial origin. They may be genome sequences, cDNA, RNA, hybrid sequences or synthetic or semi-synthetic sequences. These sequences may be obtained either by screening DNA banks (cDNA bank, genomic DNA bank), or by chemical synthesis, or by mixed methods including chemical or enzymatic modification of sequences obtained by screening banks.

The products according to the present invention may be used in the therapeutic field: in particular, the peptides according to the invention, since they are capable of modulating the activity of ras proteins, allow intervention in the process of development of cancers, and in particular they may inhibit the activity of oncogenes whose transformation activity proceeds by a functional p21-GAP interaction. Several cancers in fact have been associated with the presence of oncogenic ras proteins. Among the cancers which most often include mutated ras genes, there may be mentioned in particular adenocarcinomas of the pancreas, 90% of which have a Ki-ras oncogene mutated on the twelfth codon (Almoguera et al., Cell 53 (1988) 549), adenocarcinomas of the colon and cancers of the thyroid (50%), or carcinomas of the lung and myeloid leukaemias (30%, Bos, J. L., Cancer Res. 49 (1989) 4682).

The invention thus also relates to any pharmaceutical composition comprising, as the active principle, at least one peptide and/or one antisense oligonucleotide and/or one nucleic sequence according to the present invention. The pharmaceutical compositions according to the invention may be formulated for administration topically, orally, parenterally, intranasally, intravenously, intramuscularly, subcutaneously, intraocularly and the like. The pharmaceutical compositions preferably comprise vehicles which are pharmaceutically acceptable for an injectable formulation.

These may be, in particular, saline (monosodium or disodium phosphate, sodium, potassium, calcium or magnesium chloride and the like, or mixtures of such salts), sterile or isotonic solutions, or dry compositions, in particular lyophilizates, which allow constitution of injectable solutions by addition of sterilized water or physiological serum, as required. The doses of active principle (peptide, nucleic sequence or vector) used for the administration may be adapted as a function of various parameters, and in particular as a function of the mode of administration used, of the pathology in question, of the gene to be expressed, or else of the required duration of treatment. Generally, as regards recombinant viruses according to the invention, these are formulated and administered in the form of doses of between $10^4$ and $10^{14}$ pfu/ml, and preferably $10^6$ to $10^{10}$ pfu/ml. The term pfu ("plaque forming unit") corresponds to the infectious power of a solution of virus and is determined by infection of a suitable cell culture and measurement, generally after 48 hours, of the number of infected cell plaques. The techniques for determination of the pfu level of a viral solution are well documented in the literature.

The pharmaceutical compositions are more particularly intended for use in the treatment of cancers. More particularly, the pharmaceutical compositions comprise at least one virus in which at least one nucleotide sequence as described above is incorporated. Other advantages of the present invention will become apparent on reading the examples which follow, which should be considered as illustrative and non-limiting.

GENERAL CLONING TECHNIQUES

Figure 1:
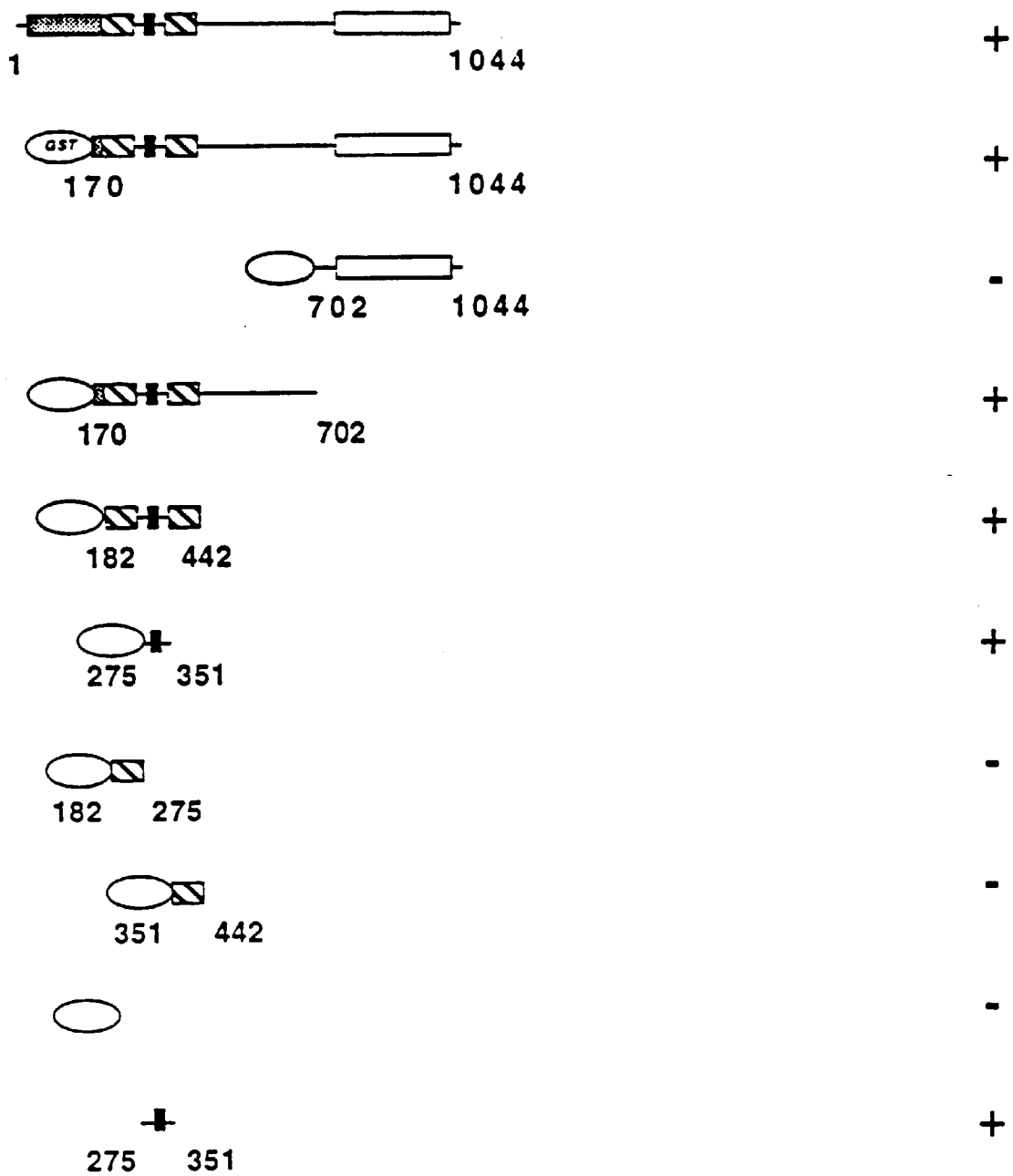
FIG. 1: Demonstration of the effector region of the protein GAP.

The methods conventionally used in molecular biology, such as preparative extraction of plasmid DNA, centrifugation of plasmid DNA in a gradient of caesium chloride, electrophoresis over agarose gel or acrylamide gel, purification of DNA fragments by electroelution, extraction of proteins with phenol or phenol/chloroform, precipitation of DNA in a saline medium with ethanol or isopropanol, transformation in *Escherichia coli* and the like, are well known to the expert and are described in abundance in the literature [Maniatis T. et al., "Molecular Cloning, a Laboratory Manual", Cold Spring Harbor Laboratory, Cold Spring Harbor, N.Y., 1982; Ausubel F. M. et al. (editors), "Current Protocols in Molecular Biology", John Wiley & Sons, New York, 1987].

The restriction enzymes were supplied by New England Biolabs (Biolabs), Bethesda Research Laboratories (BRL) or Amersham and are used in accordance with the suppliers' recommendations.

The plasmids of the type pBR322, pUC, lgt11, pGEX 2T and the phages of the series M13 are of commercial origin.

For the ligations, the DNA fragments are separated according to their size by electrophoresis in agarose gel or acrylamide gel, extracted with phenol or with a phenol/chloroform mixture, precipitated with ethanol and incubated in the presence of DNA ligase of the phage T4 (Biolabs) in accordance with the supplier's recommendations.

Filling-in of the proeminent 5' ends is effected by the Klenow fragment of DNA polymerase I of *E. coli* (Biolabs) in accordance with the supplier's specifications. Destruction of the proeminent 3' ends is effected in the presence of the DNA polymerase of the phage T4 (Biolabs) used in accordance with the manufacturer's recommendations. Destruction of the proeminent 5' ends is effected by controlled treatment with the nuclease S1.

The mutagenesis carried in vitro by synthetic oligodeoxynucleotides is effected in accordance with the method developed by Taylor et al. [Nucleic Acids Res. 13 (1985) 8749–8764] using the kit distributed by Amersham.

The enzymatic amplification of the DNA fragments by the so-called PCR technique [Polymerase-catalysed Chain Reaction, Saiki R. K. et al., Science 230 (1985) 1350–1354; Mullis K. B. and Faloona F. A., Meth. Enzym. 155 (1987) 335–350] is effected using a "DNA thermal cycler" (Perkin Elmer Cetus) in accordance with the manufacturer's specifications.

The verification of the nucleotide sequences is effected by the method developed by Sanger et al. [Proc. Natl. Acad. Sci. USA, 74 (1977) 5463–5467] using the kit distributed by Amersham.

For the hybridization experiments, the usual conditions of stringence are generally the following: hybridization: 3×SCC in the presence of 5×Denhart's at 65° C.; washing: 0.5×SSC at 65° C.

EXAMPLE 1

Demonstration of Effector Regions

The existence of effector regions within the protein GAP was demonstrated by demonstrating that anti-GAP antibodies were capable of blocking the transformation activity of ras (E.1.1.), whereas these same antibodies did not modify the interaction of GAP-ras (E.1.2.).

E.1.1. Inhibition of the ras function by anti-GAP antibodies.

Monoclonal murine antibodies directed against the protein GAP were obtained from M. Thang (Inserm U245, Hôpital St. Antoine, Paris). These antibodies were used to demonstrate the role of the GAP-p21 interaction and, more precisely, to show the influence of inhibition of this interaction on maturation of Xenopus eggs induced by ras.

*Xenopus laevis* frogs were obtained from CNRS (Montpellier, France). The frogs are anaesthetized in ice-water and fragments of the ovaries are removed surgically and transferred to a modified Barth medium (Hirai et al., Dev. Biol. 100 (1984) 214). The stage VI oocytes are recovered by agitating the oocyte aggregates for 2 hours at ambient temperature in the presence of 2 mg/ml of collagenase (Sigma). For analysis of the maturation induced by ras, 40 nl of the protein in modified Barth medium are introduced into the cytoplasm of the oocytes by microinjection, either alone or in the presence of various concentrations of anti-GAP antibodies. For analysis of the maturation induced by hormones, the oocytes are incubated in the presence of insulin (10 µg/ml) and zinc chloride (10 µM) (bovine pancreatic insulin, Sigma) or progesterone (1 µM). The oocytes are kept at 20° C. in modified Barth medium, and the 1% germinal vesicle breakdown (GVBD) is determined after incubation for 18 hours by dissection of the oocytes, which have been fixed beforehand in the presence of 5% of trichloroacetic acid. The results are expressed by the % GVBD on groups of oocytes.

The results obtained show that certain anti-GAP antibodies are capable of inhibiting the transformation activity of the ras protein. The antibody Ac200 was used subsequently to the study.

E.1.2. Absence of an effect of the Ac200 antibody on the GAP-p21 interaction The interaction between GAP and the complex p21-GTP is determined in accordance with the following protocol. The normal protein Ha-ras p21 (Rey et al., Mol. Cell. Biol. 9 (1989) 3904) is equilibrated with an excess of ($\gamma$-$^{32}$P) GTP (3000 Ci/mmol, Dupont, NEN Research Products, Boston, Mass.) in a buffer of Tris-HCl 20 mM (pH 7.5), 100 mM $(NH_4)_2SO_4$, 10 mM dithiothreitol, 1 mM $MgCl_2$ and 50 mg/ml of bovine serum albumin for 30 minutes at 30° C. The incubation is stopped by applying the cooled solution to a PD10 column (Pharmacia) equilibrated by a buffer of Tris-HCl 20 mM (pH 7.5), 10 mM dithiothreitol, 10 mM $MgCl_2$ and 1 mM phenylmethylsulphonyl fluoride, to eliminate the free nucleotides. The GTPase reaction is a variant of that described by Cassel and Selinger (Biochim. Biophys. Acta 452 (1976) 538). The reaction is started by addition of 10 $\mu$l (15 $\mu$g) of cytosol obtained by sonic treatment of strains of *E. coli* which express GAP (cf. Example E.2.1. below for the production of GAP) to 1 pmol of Ha-ras p21-($g^{-32}$P) GTP in the buffer Tris-HCl 20 mM (pH 7.5), NaCl 100 mM, dithiothreitol 10 mM, $MgCl_2$ 5 mM, GTP 100 $\mu$M and BSA 50 $\mu$g/ml, to obtain a final volume of 50 $\mu$l. The reaction is carried out for 3 minutes at 30° C. and stopped over ice by addition of 950 $\mu$l of 20 mM phosphoric acid (pH 2.3) containing 5% (w/v) of activated charcoal. After centrifugation at 1800 g, the radioactivity is measured in samples of 200 $\mu$l of the supernatant. The results are shown below.

| Product tested | Relative GAP activity |
|---|---|
| None | 100 |
| Ac200 | 100 |
| [275–351] GAP | 100 |
| Ac Y13-259 | 5 |

They show that the Ac200antibody does not modify the GAP-p21 interaction. The same test carried out with the fragment 273–351 of GAP (SEQ ID No. 1) also demonstrates that this polypeptide does not modify the functional interaction of GAP-p21.

EXAMPLE 2

Characterization of the Effector Region

E.2.1. Demonstration of a region of about 80 aa by fragmentation of GAP, production of these GAP fragments in the form of GST fusion, and reactivity towards the neutralizing antibody Ac200.

The DNA sequence coding for the protein GAP was fragmented by enzymatic digestion and the fragments obtained were separated by electroelution and brought into the form of BamHI-EcoRI fragments. These fragments were then expressed in the *E. coli* strain TG1 in the form of fusion proteins with glutathione S-transferase (GST) in accordance with the technique described by Smith and Johnson (Gene 67 (1988) 31). For this, the various fragments of DNA obtained were inserted into the BamHI-EcoRI sites of the vector pGEX 2T (Pharmacia), in 3' and in phase of a cDNA coding for GST. The vectors thus obtained are then used for transformation of the *E. coli* strain TG1. The cells thus transformed are precultured for one night at 37° C., diluted to 1/10 in LB medium, IPTG is added to induce expression (2 hours, 25° C.) and the cells are then cultured for about 25° C. at 21 hours. The cells are then lysed and the fusion proteins produced are purified by affinity over a column of Agarose-GSH. For this, the bacterial lysate is incubated in the presence of the gel (prepared and equilibrated with the lysis buffer) for 15 minutes at 4° C. After 3 washes with a buffer of Tris-HCl pH 7.4, the proteins are eluted in the presence of a buffer of Tris-HCl pH 7.7 containing an excess of GSH. The supernatant is collected and centrifuged.

The fragments thus obtained are tested as a function of their recognition by the Ac200antibody. The results obtained are shown in FIG. 1. They show that the effector region of the protein GAP is situated between about the residues 275 and 350.

E.2.2. More precise identification by "epitope scanning"

The technique of "epitope scanning" is based on the principle that a given antibody may react with peptides of 5 to 15 amino acids. As a result, identification of sequential epitopes may be achieved by preparing a complete set of overlapping peptides, of 5–15 amino acids, corresponding to the complete sequence of the antigen under consideration. This technique was used to determine the functional epitopes of the GAP fragment demonstrated in Example E.2.1. above. For this, the entire fragment was explored by sequential overlaps, by synthesis of a decapeptide for every 2 amino acids.

a) Synthesis of the overlapping peptides 35 peptides covering all the sequence SEQ ID No. 2 were synthesized chemically. The synthesis was carried out in duplicate on 2 independent supports by the method of Fmoc/t-butyl over a solid phase (kit from Cambridge Research Biochemicals).

b) Demonstration of functional epitopes

The functional epitopes recognized by the Ac200antibody were revealed in an ELISA test by an anti-murine rabbit antibody coupled to peroxidase. The chromogenic substrate of the enzyme used is amino-di-(3-ethylbenzothiazoline sulphonate) (ABTS).

Figure 2:
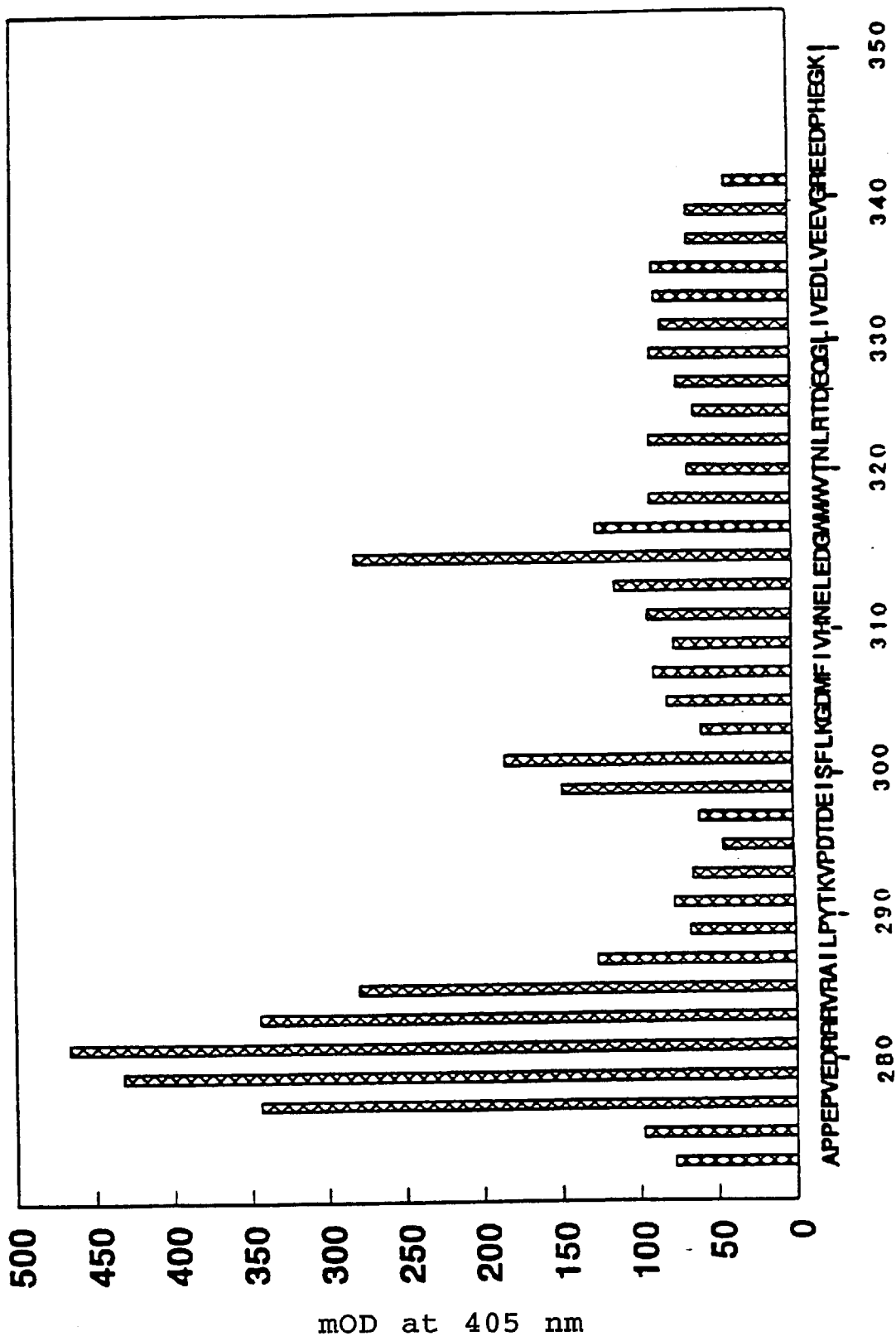
FIG. 2: Antigenic profile of the peptide SEQ ID No. 2 screened by sequential overlapping by the antibody Ac200.

The results obtained are shown on FIG. 2. The epitopes recognized by this antibody are the following:

| | |
|---|---|
| PVEDRRRVRAI | (P1) SEQ ID No 10 |
| EISF | (P2) SEQ ID NO 11 |
| EDGWM | (P3) SEQ ID NO 12 |

It is understood that other functional regions of the sequence SEQ ID No. 2 may be demonstrated using other anti-GAP antibodies.

On the basis of these results and using the same technique of chemical synthesis, the following peptides were synthesized:

| | |
|---|---|
| APPEPVEDRRRVRAILPYTKVPDTDEISFLXGD | (P4) |
| WMWVTNLRTD | (P5) |
| ISFLKGDMFIVHNELEDGWMWVTNLRTD | (P6) |
| VTNLRTDEQGLIVEDLVEEVGREEDPHEGKI | (P7) |
| PPEPVEDRRRVRAILPYTKVPDTDEIS-FLKGDMFIVHNELEDGWMWVTNLRTD | (P8) |
| Peptide SEQ ID No. 4 | (P9) |

EXAMPLE 3

Bioloaical Characterization

E.3.1. The biological activity of the peptides according to the invention was studied by measuring their effect on the maturation of Xenopus eggs induced by p21 ras Lys12, by insulin or by progesterone.

Figure 3:
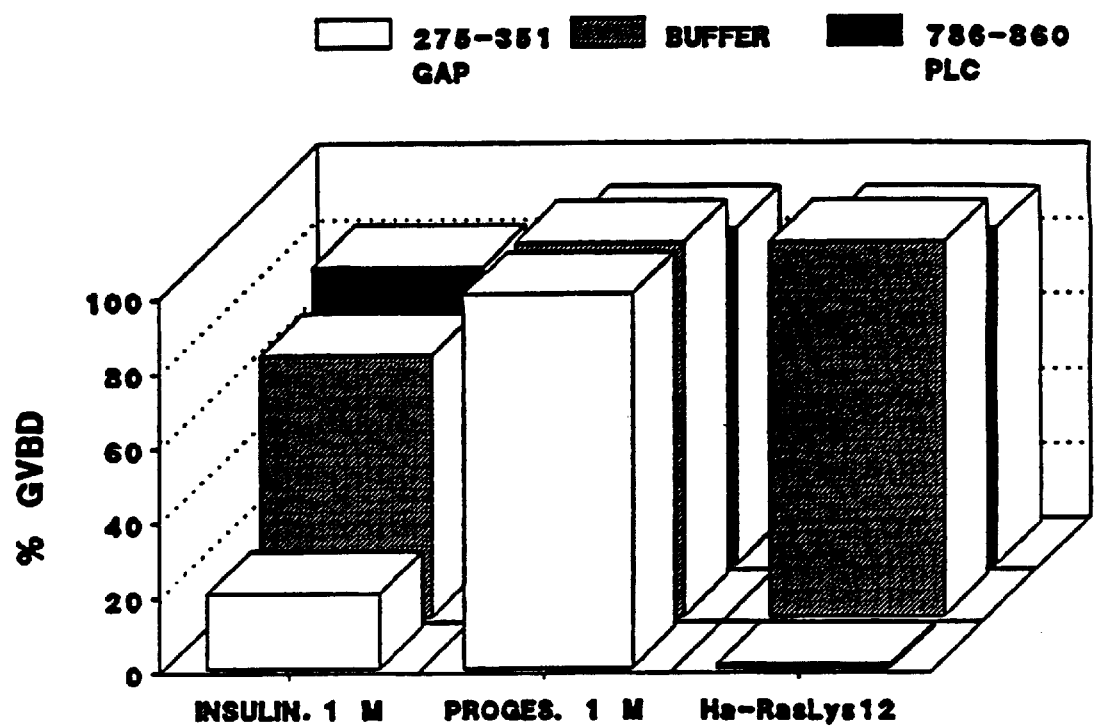
FIG. 3: Effect of peptides according to the invention on the maturation of Xenopus eggs induced by p21 Ras Lys12, insulin or progesterone.

The protocol used is the same as that described in Example E.1.1. above. The activity is measured by microinjection into the cytoplasm of the oocytes of 40 nl of the ras p21 protein in modified Barth medium, either alone or in the presence of various peptides according to the invention in varying concentrations. The results are expressed by the % of GVBD over the groups of oocytes. The results are shown on FIG. 3.

These results clearly show that the peptides according to the invention, in particular the peptide SEQ ID No. 2 and the peptide (P5), are capable of inhibiting the transformation activity of the ras protein. A fragment of identical length ([768–860] PLCγ) prepared by the same techniques from type γ human phospholipase C does not have the activity of the peptide according to the invention.

E.3.2. The peptide P9 was purified in the form of a fusion protein with GST in accordance with the protocol described in Example E.2.1., and was then separated from the GST after proteolytic cleavage with thrombin. The peptide P9 thus obtained was then tested on the maturation of Xenopus eggs under the conditions of Example E.3.1. The results obtained show that the P9 peptide completely blocks maturation of ovocytes.

The activity of P9 was then evaluated in a test for formation of foci of transformed cells. The cancerous cells in fact have the property of forming transformation foci, and in particular fibroblasts NIH 3T3 expressing an oncogenic ras. The cells NIH 3T3 were cultured in DMEM medium (Dulbecco's modified Eagle medium) comprising 10% of foetal calf serum at 37° C. in a humid environment containing 5% of $CO_2$. The plasmids pSV2-GAP and pSV2-P9 were constructed by inserting the nucleotide sequences coding for GAP and for P9 (SEQ ID No. 4) into the vector SV2. The cells NIH 3T3 were cotransfected with an oncogenic ras Ha-ras Va112, the plasmide indicated in the table, and a 10-fold excess of the gene having resistance to neomycin by the technique of transfection with cationic lipids (Schweighoffer et al., Science 256 (1992) 825). The same amount of total DNA is transfected for each dish. 24 hours after transfection, the transfected cells originating from each Petri dish (100 mm) are divided in a ratio of 1 to 10 and cultured in the same medium but in the presence of G418 (Gibco/BRL) in an amount of 0.4 mg/ml of medium. The number of transformation foci obtained per μg of transfected DNA is compatibilized after culture for 14 days. The results obtained are shown in the following table. They represent the mean of four independent tests.

| Transfected plasmids | Number of foci per μg of transfected DNA |
|---|---|
| Ha-Ras Val 12 | 110 |
| Ha-Ras Val 12 + pSV2-GAP | 120 |
| Ha-Ras Val 12 + pSV2-P9 | 35 |

These results clearly demonstrate that the peptides according to the invention (in particular peptide P9) are capable of very greatly reducing the transforming power of an oncogenic ras gene.

E.3.3. In vivo antitumoral activity a) Preparation of a recombinant virus comprising a nucleic sequence according to the invention.

Defective recombinant viruses according to the invention may be prepared by homologous recombination between a defective virus and a plasmid carrying, inter alia, the nucleic acid sequence as defined above (Levrero et al., Gene 101 (1991) 195; Graham, EMBO J. 3(12) (1984) 2917). Homologous recombination occurs after cotransfection of the said virus and plasmid in a suitable cell line. The cell line used should preferably (i) be transformable by the said elements and (ii) comprise sequences which are capable of complementing the part of the genome of the defective virus, preferably in integrated form to avoid the risk of recombination. An example which may be mentioned of a line which can be used for preparation of defective recombinant adenoviruses is the human embryo kidney line 293 (Graham et al., J. Gen. Virol. 36 (1977) 59) which contains, in particular, integrated into its genome, the left-hand part of the genome of an adenovirus Ad5 (12%). An example which may be mentioned of a line which can be used for preparation of defective recombinant retroviruses is the line CRIP (Danos and Mulligan, PNAS 85 (1988) 6460).

The viruses which have multiplied are then recovered and purified in accordance with the conventional techniques of molecular biology.

The sequence SEQ ID No. 3 coding for the peptide P9 was cloned in a neo-plasmid under the control of an early promoter of SV40. The cassette promoter SV40-SEQ ID No. 3 was then cloned in a retroviral vector of the Moloney type (Palmer et al., PNAS 84 (1987) 1055). A control vector was also constructed, in which the fragment was inserted in the antisense orientation.

The amphotrophic cells GP+envAm12 were transfected with the retroviral vectors described above by the technique with calcium phosphate (Markowitz et al., Virology 167 (1988) 400; Graham et al., Virology 52 (1973) 456). 48 hours after the transfection, the transfected cells are subcultured in a medium containing G418 (Gibco, BRL) in a concentration of 0.4 mg/ml. Two weeks later, the colonies resistant to G418 are cultured in a large quantity. The transfected cells having a high level of virus are cocultured with the ecotropic Psi2 packaging cells in order to increase the level of virus (Palmer et al., PNAS 84 (1987) 1055).

The recombinant viruses thus produced are isolated by the conventional techniques of molecular biology.

b) In vivo antitumoral activity

A model of a pulmonary tumour in mice was developed in accordance with the technique described by McLemore et al. (Cancer Res. 47 (1987) 5132). For this, the mice receive $10^5$ cells of H460a intratracheally. On days 4, 5 and 6, the mice which have received the tumour are treated by the same intratracheal route with 0.1 ml of viral suspension obtained above (about $5 \cdot 10^6$ cpu/ml) containing 5 μg/ml of protamine. 30 days after inoculation of the tumour, the mice are analysed for the presence of tumours, the volume of which is determined approximately in accordance with the above-mentioned technique described by McLemore et al. The animals treated with the virus P9 have no measurable tumours, or only tumours of very small size. Conversely, the animals treated with the same viral level of antisense virus P9 are indistinguishable from the control animals which have received only the tumour.

These results clearly show that the sequences according to the invention, in particular in the form of viral vectors, may be used in vivo for the treatment of cancers.

It is understood that the expert may use other viruses for the transfer of the peptides according to the invention in vivo. In particular, these may be adenoviruses, adeno-associated viruses, herpes viruses and the like. Vectors derived from these viruses have been described in the prior art and construction of viruses according to the invention may be carried out by the expert on the basis of his general knowledge (cf. in particular Akli et al., Nature Genetics 3 (1993) 224; Stratford-Perricaudet et al., Human Gene Therapy 1 (1990) 241; EP 185 573, Levrero et al., Gene 101 (1991) 195; WO 91/1808; EP 243204).

What is claimed is:

1. A peptide comprising a non-functional effector region of protein GAP, wherein the peptide inhibits transformation activity of activated p21 proteins.

2. The peptide according to claim 1, wherein the activated p21 proteins are p21-GTP-GAP complexes.

3. The peptide according to claim 2, wherein the peptide binds p21 protein.

4. The peptide according to claim 1 modified by a membrane-directing sequence of type CAAX, where C is a cysteine, A is an aliphatic amino acid and X is any amino acid.

5. A nucleic acid coding for a peptide according to claim 1.

6. A viral vector comprising a nucleic acid according to claim 5.

7. An oligonucleotide that hybridizes with the nucleic acid according to claim 5 or its complement.

8. A pharmaceutical composition comprising a pharmaceutically effective amount of at least one peptide according to claim 1.

9. A pharmaceutical composition comprising a nucleic acid according to claim 5.

10. A pharmaceutical composition according to claim 9, wherein said nucleic acid is incorporated in a recombinant virus.

11. A pharmaceutical composition according to claim 10, wherein the virus is selected from the group consisting of retroviruses and adenoviruses.

12. A pharmaceutical composition according to claim 8 wherein said amount is effective for the treatment of cancers.

13. A replication defective recombinant virus comprising a heterologous nucleic acid coding for a peptide according to claim 1.

14. The virus according to claim 13, wherein the virus is an adenovirus, a retrovirus, an adeno-associated virus or herpes virus.

15. A process for the preparation of a peptide according to claim 1 comprising introducing a nucleotide sequence encoding a peptide according to claim 1 into a host cell, culturing said cell under conditions permitting expression of said sequence and recovery of the peptide produced.

16. The peptide according to claim 2 that binds p21-GTP-GAP complex.

17. The pharmaceutical composition according to claim 10, comprising between $10^4$ to $10^{14}$ pfu/ml of recombinant virus.

18. A peptide comprising at least a nonfunctional portion of the effector region of protein GAP, wherein the peptide inhibits transformation activity of activated p21 proteins.

19. The peptide according to claim 18, selected from the group consisting of:

P1 (SEQ ID NO: 10),
P2 (SEQ ID NO: 11),
P3 (SEQ ID NO: 12),
P4 (SEQ ID NO: 5),
P5 (SEQ ID NO: 6),
P6 (SEQ ID NO: 7),
P7 (SEQ ID NO: 8),
P8 (SEQ ID NO: 9),
P9 (SEQ ID NO: 4), and
a peptide having the sequence SEQ ID NO: 2.

20. The peptide according to claim 18, wherein the activated p21 proteins are p21-GTP-GAP complexes.

21. The peptide according to claim 18, wherein the peptide binds p21 protein.

22. The peptide according to claim 18 that binds p21-GTP-GAP complex.

23. A nucleic acid coding for a peptide according to claim 18.

24. A viral vector comprising a nucleic acid according to claim 23.

25. A replication defective recombinant virus comprising a heterologous nucleic acid coding for a peptide according to claim 18.

26. The virus according to claim 25, wherein the virus is an adenovirus, a retrovirus, an adeno-associated virus or herpes virus.

27. An oligonucleotide that hybridizes with the nucleic acid according to claim 23 or its complement.

28. A pharmaceutical composition comprising a pharmaceutically effective amount of at least one peptide according to claim 18.

29. A pharmaceutical composition comprising a nucleic acid according to claim 23.

30. The pharmaceutical composition according to claim 29, wherein said nucleic acid is incorporated in a recombinant virus.

31. The pharmaceutical composition according to claim 30, wherein the virus is selected from the group consisting of retroviruses and adenoviruses.

32. The pharmaceutical composition according to claim 28, wherein said amount is effective for the treatment of cancers.

33. The pharmaceutical composition according to claim 29, comprising between $10^4$ to $10^{14}$ pfu/ml of recombinant virus.

34. A process for the preparation of a peptide according to claim 18 comprising introducing a nucleotide sequence encoding a peptide according to claim 18 into a host cell, culturing said cell under conditions permitting expression of said sequence and recovery of the peptide produced.

35. A GAP protein derivative comprising a non-functional effector region.

36. A nucleic acid encoding a GAP protein derivative according to claim 35.

37. A vector comprising a nucleic acid according to claim 36.

38. A recombinant virus comprising a heterologous nucleic acid coding for a GAP protein derivative according to claim 35.

39. The virus according to claim 38, wherein the virus is an adenovirus, a retrovirus, an adeno-associated virus or herpes virus.

40. A pharmaceutical composition comprising a pharmaceutically effective amount of a GAP protein derivative according to claim 35.

41. A pharmaceutical composition comprising a nucleic acid according to claim 36.

42. The pharmaceutical composition according to claim 41, wherein said nucleic acid is incorporated in a recombinant virus.

43. The pharmaceutical composition according to claim 42, wherein the virus is selected from the group consisting of retroviruses and adenoviruses.

44. The pharmaceutical composition according to claim 40 wherein said amount is effective for the treatment of cancers.

* * * * *

UNITED STATES PATENT AND TRADEMARK OFFICE
CERTIFICATE OF CORRECTION

PATENT NO.: 6,180,362 B1

DATED: January 30, 2001

INVENTORS: Duchesne *et al.*

It is hereby certified that errors appear in the above-identified patent and that said Letters Patent is hereby corrected as shown below:

Claim 7, col. 23, line 49: after "complement" insert --and does not hybridize to a nucleic acid encoding a functional effector region of protein GAP--; and Claim 27, col. 25, line 10: after "complement" insert --and does not hybridize to a nucleic acid encoding a functional effector region of protein GAP--.

Signed and Sealed this

Fifteenth Day of May, 2001

*Attest:*

NICHOLAS P. GODICI

*Attesting Officer*    Acting Director of the United States Patent and Trademark Office

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 234 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Homo sapiens (ix) FEATURE:
      (A) NAME/KEY: CDS
      (B) LOCATION: 1..234

(xi) SEQUENCE DESCRIPTION: SEQ ID NO:1:

```
GCA CCA CCA GAG CCA GTA GAA GAT AGA AGG CGT GTA CGA GCT ATT CTA      48
Ala Pro Pro Glu Pro Val Glu Asp Arg Arg Arg Val Arg Ala Ile Leu
 1               5                  10                  15

CCT TAC ACA AAA GTA CCA GAC ACT GAT GAA ATA AGT TTC TTA AAA GGA      96
Pro Tyr Thr Lys Val Pro Asp Thr Asp Glu Ile Ser Phe Leu Lys Gly
             20                  25                  30

GAT ATG TTC ATT GTT CAT AAT GAA TTA GAA GAT GGA TGG ATG TGG GTT     144
Asp Met Phe Ile Val His Asn Glu Leu Glu Asp Gly Trp Met Trp Val
         35                  40                  45

ACA AAT TTA AGA ACA GAT GAA CAA GGC CTT ATT GTT GAA GAC CTA GTA     192
Thr Asn Leu Arg Thr Asp Glu Gln Gly Leu Ile Val Glu Asp Leu Val
     50                  55                  60

GAA GAG GTG GGC CGG GAA GAA GAT CCA CAT GAA GGA AAA ATA             234
Glu Glu Val Gly Arg Glu Glu Asp Pro His Glu Gly Lys Ile
 65                  70                  75
```

(2) INFORMATION FOR SEQ ID NO:2:

(i) SEQUENCE CHARACTERISTICS:
      (A) LENGTH: 78 amino acids
      (B) TYPE: amino acid
      (D) TOPOLOGY: linear (ii) MOLECULE TYPE: protein (xi) SEQUENCE DESCRIPTION: SEQ ID NO:2:

```
Ala Pro Pro Glu Pro Val Glu Asp Arg Arg Arg Val Arg Ala Ile Leu
 1               5                  10                  15

Pro Tyr Thr Lys Val Pro Asp Thr Asp Glu Ile Ser Phe Leu Lys Gly
             20                  25                  30

Asp Met Phe Ile Val His Asn Glu Leu Glu Asp Gly Trp Met Trp Val
         35                  40                  45

Thr Asn Leu Arg Thr Asp Glu Gln Gly Leu Ile Val Glu Asp Leu Val
     50                  55                  60

Glu Glu Val Gly Arg Glu Glu Asp Pro His Glu Gly Lys Ile
 65                  70                  75
```

(2) INFORMATION FOR SEQ ID NO:3:

(i) SEQUENCE CHARACTERISTICS:
      (A) LENGTH: 1548 base pairs (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION: 1..1548

(xi) SEQUENCE DESCRIPTION: SEQ ID NO:3:

```
GGC GGC GGT TTT CCC CCT CTG CCC CCT CCC CCT TAC CTG CCC CCT TTG      48
Gly Gly Gly Phe Pro Pro Leu Pro Pro Pro Pro Tyr Leu Pro Pro Leu
  1               5                  10                  15

GGG GCG GGC CTC GGG ACA GTG GAC GAA GGT GAC TCT CTG GAT GGA CCA      96
Gly Ala Gly Leu Gly Thr Val Asp Glu Gly Asp Ser Leu Asp Gly Pro
             20                  25                  30

GAA TAC GAG GAG GAA GAG GTG GCC ATA CCG TTG ACC GCT CCT CCA ACT     144
Glu Tyr Glu Glu Glu Glu Val Ala Ile Pro Leu Thr Ala Pro Pro Thr
         35                  40                  45

AAC CAG TGG TAT CAC GGA AAA CTT GAC AGA ACG ATA GCA GAA GAA CGC     192
Asn Gln Trp Tyr His Gly Lys Leu Asp Arg Thr Ile Ala Glu Glu Arg
     50                  55                  60

CTC AGG CAG GCA GGG AAG TCT GGC AGT TAT CTT ATA AGA GAG AGT GAT     240
Leu Arg Gln Ala Gly Lys Ser Gly Ser Tyr Leu Ile Arg Glu Ser Asp
 65                  70                  75                  80

CGG AGG CCA GGG TCC TTT GTA CTT TCA TTT CTT AGC CAG ATG AAT GTT     288
Arg Arg Pro Gly Ser Phe Val Leu Ser Phe Leu Ser Gln Met Asn Val
                 85                  90                  95

GTC AAC CAT TTT AGG ATT ATT GCT ATG TGT GGA GAT TAC TAC ATT GGT     336
Val Asn His Phe Arg Ile Ile Ala Met Cys Gly Asp Tyr Tyr Ile Gly
            100                 105                 110

GGA AGA CGT TTT TCT TCA CTG TCA GAC CTA ATA GGT TAT TAC AGT CAT     384
Gly Arg Arg Phe Ser Ser Leu Ser Asp Leu Ile Gly Tyr Tyr Ser His
        115                 120                 125

GTT TCT TGT TTG CTT AAA GGA GAA AAA TTA CTT TAC CCA GTT GCA CCA     432
Val Ser Cys Leu Leu Lys Gly Glu Lys Leu Leu Tyr Pro Val Ala Pro
130                 135                 140

CCA GAG CCA GTA GAA GAT AGA AGG CGT GTA CGA GCT ATT CTA CCT TAC     480
Pro Glu Pro Val Glu Asp Arg Arg Arg Val Arg Ala Ile Leu Pro Tyr
145                 150                 155                 160

ACA AAA GTA CCA GAC ACT GAT GAA ATA AGT TTC TTA AAA GGA GAT ATG     528
Thr Lys Val Pro Asp Thr Asp Glu Ile Ser Phe Leu Lys Gly Asp Met
                165                 170                 175

TTC ATT GTT CAT AAT GAA TTA GAA GAT GGA TGG ATG TGG GTT ACA AAT     576
Phe Ile Val His Asn Glu Leu Glu Asp Gly Trp Met Trp Val Thr Asn
            180                 185                 190

TTA AGA ACA GAT GAA CAA GGC CTT ATT GTT GAA GAC CTA GTA GAA GAG     624
Leu Arg Thr Asp Glu Gln Gly Leu Ile Val Glu Asp Leu Val Glu Glu
        195                 200                 205

GTG GGC CGG GAA GAA GAT CCA CAT GAA GGA AAA ATA TGG TTC CAT GGG     672
Val Gly Arg Glu Glu Asp Pro His Glu Gly Lys Ile Trp Phe His Gly
    210                 215                 220

AAG ATT TCC AAA CAG GAA GCT TAT AAT TTA CTA ATG ACA GTT GGT CAA     720
Lys Ile Ser Lys Gln Glu Ala Tyr Asn Leu Leu Met Thr Val Gly Gln
225                 230                 235                 240

GTC TGC AGT TTT CTT GTG AGG CCC TCA GAT AAT ACT CCT GGC GAT TAT     768
Val Cys Ser Phe Leu Val Arg Pro Ser Asp Asn Thr Pro Gly Asp Tyr
                245                 250                 255
```

```
TCA CTT TAT TTC CGG ACC AAT GAA AAT ATT CAG CGA TTT AAA ATA TGT         816
Ser Leu Tyr Phe Arg Thr Asn Glu Asn Ile Gln Arg Phe Lys Ile Cys
        260                 265                 270

CCA ACG CCA AAC AAT CAG TTT ATG ATG GGA GGC CGG TAT TAT AAC AGC         864
Pro Thr Pro Asn Asn Gln Phe Met Met Gly Gly Arg Tyr Tyr Asn Ser
        275                 280                 285

ATT GGG GAC ATC ATA GAT CAC TAT CGA AAA GAA CAG ATT GTT GAA GGA         912
Ile Gly Asp Ile Ile Asp His Tyr Arg Lys Glu Gln Ile Val Glu Gly
        290                 295                 300

TAT TAT CTT AAG GAA CCT GTA CCA ATG CAG GAT CAA GAA CAA GTA CTC         960
Tyr Tyr Leu Lys Glu Pro Val Pro Met Gln Asp Gln Glu Gln Val Leu
305                 310                 315                 320

AAT GAC ACA GTG GAT GGC AAG GAA ATC TAT AAT ACC ATC CGT CGT AAA         1008
Asn Asp Thr Val Asp Gly Lys Glu Ile Tyr Asn Thr Ile Arg Arg Lys
                325                 330                 335

ACA AAG GAT GCC TTT TAT AAA AAC ATT GTT AAG AAA GGT TAT CTT CTG         1056
Thr Lys Asp Ala Phe Tyr Lys Asn Ile Val Lys Lys Gly Tyr Leu Leu
                340                 345                 350

AAA AAG GGC AAA GGA AAA CGT TGG AAA AAT TTA TAT TTT ATC TTA GAG         1104
Lys Lys Gly Lys Gly Lys Arg Trp Lys Asn Leu Tyr Phe Ile Leu Glu
                355                 360                 365

GGT AGT GAT GCC CAA CTT ATT TAT TTT GAA AGC GAA AAA CGA GCT ACC         1152
Gly Ser Asp Ala Gln Leu Ile Tyr Phe Glu Ser Glu Lys Arg Ala Thr
        370                 375                 380

AAA CCA AAA GGA TTA ATA GAT CTC AGT GTA TGT TCT GTC TAT GTC GTT         1200
Lys Pro Lys Gly Leu Ile Asp Leu Ser Val Cys Ser Val Tyr Val Val
385                 390                 395                 400

CAT GAT AGT CTC TTT GGC AGG CCA AAC TGT TTT CAG ATA GTA GTT CAG         1248
His Asp Ser Leu Phe Gly Arg Pro Asn Cys Phe Gln Ile Val Val Gln
                405                 410                 415

CAC TTT AGT GAA GAA CAT TAC ATC TTT TAC TTT GCA GGA GAA ACT CCA         1296
His Phe Ser Glu Glu His Tyr Ile Phe Tyr Phe Ala Gly Glu Thr Pro
                420                 425                 430

GAA CAA GCA GAG GAT TGG ATG AAA GGT CTG CAG GCA TTT TGC AAT TTA         1344
Glu Gln Ala Glu Asp Trp Met Lys Gly Leu Gln Ala Phe Cys Asn Leu
                435                 440                 445

CGG AAA AGT AGT CCA GGG ACA TCC AAT AAA CGC CTT CGT CAG GTC AGC         1392
Arg Lys Ser Ser Pro Gly Thr Ser Asn Lys Arg Leu Arg Gln Val Ser
        450                 455                 460

AGC CTT GTT TTA CAT ATT GAA GAA GCC CAT AAA CTC CCA GTA AAA CAT         1440
Ser Leu Val Leu His Ile Glu Glu Ala His Lys Leu Pro Val Lys His
465                 470                 475                 480

TTT ACT AAT CCA TAT TGT AAC ATC TAC CTG AAT AGT GTC CAA GTA GCA         1488
Phe Thr Asn Pro Tyr Cys Asn Ile Tyr Leu Asn Ser Val Gln Val Ala
                485                 490                 495

AAA ACT CAT GCA AGG GAA GGG CAA AAC CCA GTA TGG TCA GAA GAG TTT         1536
Lys Thr His Ala Arg Glu Gly Gln Asn Pro Val Trp Ser Glu Glu Phe
                500                 505                 510

GTC TTT GAT GAT                                                          1548
Val Phe Asp Asp
        515
```

(2) INFORMATION FOR SEQ ID NO:4:

(i) SEQUENCE CHARACTERISTICS:
        (A) LENGTH: 516 amino acids
        (B) TYPE: amino acid
        (D) TOPOLOGY: linear (ii) MOLECULE TYPE: protein (xi) SEQUENCE DESCRIPTION: SEQ ID NO:4:

-continued

```
Gly Gly Gly Phe Pro Pro Leu Pro Pro Pro Tyr Leu Pro Pro Leu
 1               5                  10                  15

Gly Ala Gly Leu Gly Thr Val Asp Glu Gly Asp Ser Leu Asp Gly Pro
            20                  25                  30

Glu Tyr Glu Glu Glu Glu Val Ala Ile Pro Leu Thr Ala Pro Pro Thr
            35                  40                  45

Asn Gln Trp Tyr His Gly Lys Leu Asp Arg Thr Ile Ala Glu Glu Arg
        50                  55                  60

Leu Arg Gln Ala Gly Lys Ser Gly Ser Tyr Leu Ile Arg Glu Ser Asp
 65                  70                  75                  80

Arg Arg Pro Gly Ser Phe Val Leu Ser Phe Leu Ser Gln Met Asn Val
                85                  90                  95

Val Asn His Phe Arg Ile Ile Ala Met Cys Gly Asp Tyr Tyr Ile Gly
            100                 105                 110

Gly Arg Arg Phe Ser Ser Leu Ser Asp Leu Ile Gly Tyr Tyr Ser His
        115                 120                 125

Val Ser Cys Leu Leu Lys Gly Glu Lys Leu Leu Tyr Pro Val Ala Pro
130                 135                 140

Pro Glu Pro Val Glu Asp Arg Arg Val Arg Ala Ile Leu Pro Tyr
145                 150                 155                 160

Thr Lys Val Pro Asp Thr Asp Glu Ile Ser Phe Leu Lys Gly Asp Met
                165                 170                 175

Phe Ile Val His Asn Glu Leu Glu Asp Gly Trp Met Trp Val Thr Asn
            180                 185                 190

Leu Arg Thr Asp Glu Gln Gly Leu Ile Val Glu Asp Leu Val Glu Glu
        195                 200                 205

Val Gly Arg Glu Glu Asp Pro His Glu Gly Lys Ile Trp Phe His Gly
210                 215                 220

Lys Ile Ser Lys Gln Glu Ala Tyr Asn Leu Leu Met Thr Val Gly Gln
225                 230                 235                 240

Val Cys Ser Phe Leu Val Arg Pro Ser Asp Asn Thr Pro Gly Asp Tyr
                245                 250                 255

Ser Leu Tyr Phe Arg Thr Asn Glu Asn Ile Gln Arg Phe Lys Ile Cys
            260                 265                 270

Pro Thr Pro Asn Asn Gln Phe Met Met Gly Gly Arg Tyr Tyr Asn Ser
        275                 280                 285

Ile Gly Asp Ile Ile Asp His Tyr Arg Lys Glu Gln Ile Val Glu Gly
        290                 295                 300

Tyr Tyr Leu Lys Glu Pro Val Pro Met Gln Asp Gln Glu Gln Val Leu
305                 310                 315                 320

Asn Asp Thr Val Asp Gly Lys Glu Ile Tyr Asn Thr Ile Arg Arg Lys
                325                 330                 335

Thr Lys Asp Ala Phe Tyr Lys Asn Ile Val Lys Lys Gly Tyr Leu Leu
            340                 345                 350

Lys Lys Gly Lys Gly Lys Arg Trp Lys Asn Leu Tyr Phe Ile Leu Glu
        355                 360                 365

Gly Ser Asp Ala Gln Leu Ile Tyr Phe Glu Ser Glu Lys Arg Ala Thr
370                 375                 380

Lys Pro Lys Gly Leu Ile Asp Leu Ser Val Cys Ser Val Tyr Val Val
385                 390                 395                 400

His Asp Ser Leu Phe Gly Arg Pro Asn Cys Phe Gln Ile Val Val Gln
                405                 410                 415
```

```
His Phe Ser Glu Glu His Tyr Ile Phe Tyr Phe Ala Gly Glu Thr Pro
            420                 425                 430

Glu Gln Ala Glu Asp Trp Met Lys Gly Leu Gln Ala Phe Cys Asn Leu
            435                 440                 445

Arg Lys Ser Ser Pro Gly Thr Ser Asn Lys Arg Leu Arg Gln Val Ser
            450                 455                 460

Ser Leu Val Leu His Ile Glu Glu Ala His Lys Leu Pro Val Lys His
465                 470                 475                 480

Phe Thr Asn Pro Tyr Cys Asn Ile Tyr Leu Asn Ser Val Gln Val Ala
                    485                 490                 495

Lys Thr His Ala Arg Glu Gly Gln Asn Pro Val Trp Ser Glu Glu Phe
            500                 505                 510

Val Phe Asp Asp
            515

(2) INFORMATION FOR SEQ ID NO:5:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:5:

Ala Pro Pro Glu Pro Val Glu Asp Arg Arg Arg Val Arg Ala Ile Leu
1               5                   10                  15

Pro Tyr Thr Lys Val Pro Asp Thr Asp Glu Ile Ser Phe Leu Lys Gly
                20                  25                  30

Asp (2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:6:

Trp Met Trp Val Thr Asn Leu Arg Thr Asp
1               5                   10

(2) INFORMATION FOR SEQ ID NO:7:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:7:
```

```
Ile Ser Phe Leu Lys Gly Asp Met Phe Ile Val His Asn Glu Leu Glu
 1               5                  10                  15

Asp Gly Trp Met Trp Val Thr Asn Leu Arg Thr Asp
            20                  25
```

(2) INFORMATION FOR SEQ ID NO:8:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:8:

```
Val Thr Asn Leu Arg Thr Asp Glu Gln Gly Leu Ile Val Glu Asp Leu
 1               5                  10                  15

Val Glu Glu Val Gly Arg Glu Glu Asp Pro His Glu Gly Lys Ile
            20                  25                  30
```

(2) INFORMATION FOR SEQ ID NO:9:

(i) SEQUENCE CHARACTERISTICS:
        (A) LENGTH: 53 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:9:

```
Pro Pro Glu Pro Val Glu Asp Arg Arg Val Arg Ala Ile Leu Pro
 1               5                  10                  15

Tyr Thr Lys Val Pro Asp Thr Asp Glu Ile Ser Phe Leu Lys Gly Asp
            20                  25                  30

Met Phe Ile Val His Asn Glu Leu Glu Asp Gly Trp Met Trp Val Thr
            35                  40                  45

Asn Leu Arg Thr Asp
        50
```

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:10:

```
Pro Val Glu Asp Arg Arg Arg Val Arg Ala Ile
 1               5                  10
```

(2) INFORMATION FOR SEQ ID NO:11:

```
    (i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:11:

Glu Ile Ser Phe
1

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:12:

Glu Asp Gly Trp Met
1               5
```